United States Patent [19]

Ichii et al.

[11] Patent Number: 5,198,144

[45] Date of Patent: Mar. 30, 1993

[54] BATHING PREPARATION

[75] Inventors: Yuji Ichii; Hidenori Yorozu, both of Tochigi; Kazuyuki Fukuda; Yu Izumi, both of Chiba, all of Japan

[73] Assignee: Kao Corporation, Tokyo, Japan

[21] Appl. No.: 735,666

[22] Filed: Jul. 26, 1991

Related U.S. Application Data

[63] Continuation of Ser. No. 331,207, Mar. 31, 1989.

[30] Foreign Application Priority Data

Apr. 1, 1988 [JP] Japan .................................. 63-80451

[51] Int. Cl.$^5$ .............................................. C11D 3/50
[52] U.S. Cl. ........................... 252/174.11; 252/174.14; 252/DIG. 5; 424/715; 424/717
[58] Field of Search ............................ 424/715, 717; 252/174.11, 174.14, DIG. 5

[56] References Cited

U.S. PATENT DOCUMENTS

| | | | |
|---|---|---|---|
| 3,577,490 | 5/1971 | Welsh et al. | 264/120 |
| 4,093,745 | 6/1978 | Wood et al. | 424/358 |
| 4,380,500 | 4/1983 | Boden | 252/174.11 |
| 4,390,444 | 6/1983 | Mookherjee | 252/174.11 |
| 4,664,835 | 5/1987 | Grollier et al. | 252/90 |
| 4,678,661 | 7/1987 | Gergely et al. | 424/44 |
| 4,732,759 | 3/1988 | Shibanai et al. | 424/94.61 |

FOREIGN PATENT DOCUMENTS

| | | |
|---|---|---|
| 0142597 | 5/1985 | European Pat. Off. . |
| 0150250 | 8/1985 | European Pat. Off. . |
| 4852919 | 7/1973 | Japan . |
| 0228100 | 4/1985 | Japan . |
| 0215616 | 10/1985 | Japan . |

OTHER PUBLICATIONS

Yasuteru, E. et al., *Chemical Abstracts* 104: 74285K 377 (1986).

*Primary Examiner*—Patrick P. Garvin
*Assistant Examiner*—Brent M. Peebles
*Attorney, Agent, or Firm*—Sughrue, Mion, Zinn, Macpeak & Seas

[57] ABSTRACT

A bathing preparation comprising at least one organic acid and at least one carbonate is disclosed. This bathing preparation contains fumaric acid in an amount of 20% by weight or more of the total of the organic acid and at least one highly volatile perfume. The perfume is not vaporized into the atmosphere. Therefore, the bathing preparation sustains its aroma in bath water for a long time, thus giving improved relaxant and refreshing effects.

16 Claims, No Drawings

BATHING PREPARATION

This is a continuation of application Ser. No. 07/331,207 filed Mar. 31, 1989.

FIELD OF THE INVENTION

This invention relates to a bathing preparation comprising at least one organic acid, at least one carbonate, and at least one perfume, wherein, when dissolved in bath water, the vaporization of the perfume together with the expansion of carbon dioxide gas is inhibited so as to thereby sustain the aroma of the preparation for a prolonged period of time.

BACKGROUND OF THE INVENTION

A bathing preparation is commonly prepared by blending a mixture of inorganic salts, such as mirabilite, borax, sulfur, common salt or carbonates with, for example, perfumes, colorants, vegetable extracts and organic acids. This bathing preparation imparts an aroma and/or a color to bath water and appropriately stimulates the skin surface to thereby accelerate blood circulation and promote recovery from fatigue as well as metabolism. Expandable bathing preparations comprising at least one carbonate and at least one organic acid are known which exert improved relaxant and refreshing effects through the expansion of carbon dioxide gas in bath water, to thereby make the bath joyful.

In order to enhance the above-mentioned effects, perfumes are added to the bathing preparation. However, highly volatile perfumes scarcely give the desired effects since they are vaporized in the atmosphere together with the expansion of carbon dioxide gas.

As a result, it is proposed to use perfumes in an encapsulated or included form to thereby prevent the vaporization of the same, thus sustaining the aroma for a long period of time (cf. JP-A-62-223111 (the term "JP-A" as used herein means an "unexamined published Japanese patent application") and JP-B-52-21573-(the term "JP-B" as used herein means an "examined Japanese patent publication"). However, both encapsulation and inclusion require a troublesome procedure and a high cost. In addition to these economical disadvantages, it is difficult to form tablets of a bathing preparation comprising an encapsulated perfume.

SUMMARY OF THE INVENTION

It has been found in the present invention that an expandable bathing preparation comprising 20% by weight or more of fumaric acid as an organic acid can prevent the vaporization of particular highly volatile perfumes without requiring any encapsulation on inclusion procedure.

Accordingly, the present invention provide a bathing preparation comprising:

(A) at least one organic acid, wherein fumaric acid amounts to 20% by weight or more of the total of said organic acid, (B) at least one carbonate, and (C) at least one perfume selected from the group consisting of terpene hydrocarbons having 10 carbon atoms and formates, acetates and propionates of an alcohol having from 5 to 10 carbon atoms.

DETAILED DESCRIPTION OF THE INVENTION

The carbonates to be used in the bathing preparation of the present invention is not critical to the present invention. Examples thereof include sodium hydrogencarbonate, sodium carbonate, potassium hydrogencarbonate, potassium carbonate, calcium carbonate, magnesium carbonate and sodium sesquicarbonate. Either one of these carbonates or a mixture thereof may be used in the present invention.

The carbonate content in the bathing preparation preferably ranges from 5 to 80% by weight, more preferably from 10 to 50% by weight, based on the total composition.

The bathing preparation of the present invention should contain fumaric acid in an amount of 20% by weight or more of the total of the organic acids. Examples of other organic acids include citric acid, succinic acid, malic acid and tartaric acid. When the fumaric acid amounts to less than 20% by weight of the organic acids, the vaporization of the highly volatile perfumes cannot be inhibited. The total organic acid content preferably ranges 10 to 300% by weight, more preferably 30 to 150% by weight, based on the above-mentioned carbonates.

Fumaric acid, which is hardly soluble in water, sometimes shows floatation when dissolved in bath water. Therefore, it may be made highly soluble in water by surface-treating such with water-soluble polymers, e.g., sodium polyacrylate or sodium carboxymethyl cellulose, or hydrophilic nonionic surfactants, e.g., polyethylene glycol, sucrose fatty acid esters, polyglycerol fatty acid esters, or a mixture thereof. The water-soluble polymers and hydrophilic nonionic surfactants are preferably used in an amount of 0 to 40% by weight (more preferably 0.1 to 20% by weight) based on the fumaric acid and in an amount of 0 to 5% by weight (more preferably 0.02 to 0.1% by weight) based on the fumaric acid, respectively.

Regarding the highly volatile perfumes to be used in the present invention, examples of the terpene hydrocarbons having 10 carbon atoms include $\alpha$-pinene, $\beta$-pinene, camphene, limonene, terpinolene, myrcene and p-cymene; examples of the formates of an alcohol having from 5 to 10 carbon atoms include geranyl formate, benzyl formate and phenylethyl formate; examples of acetates of an alcohol having from 5 to 10 carbon atoms include isoamyl acetate, citronellyl acetate, geranyl acetate, benzyl acetate, linalyl acetate, phenylethyl acetate, menthyl acetate, bornyl acetate, terpenyl acetate, cinnamyl acetate, anisyl acetate and myrcenyl acetate; and examples of propionates of an alcohol having from 5 to 10 carbon atoms include linalyl propionate, citronellyl propionate, geranyl propionate, benzyl propionate, terpenyl propionate and cinnamyl propionate.

Each of these highly volatile perfumes can be used alone in the bathing preparation of the present invention. Alternatively, a mixture thereof together with other perfumes may be used. The bathing preparation of the present invention preferably comprises 0.001 to 2% by weight, more preferably 0.005 to 0.6% by weight, of the highly volatile perfume(s) based on the total composition. Further, it is preferable that the total perfumes amount to 0.2 to 2% by weight of the bathing preparation.

In addition to the above-mentioned essential components, the bathing preparation of the present invention may further contain inorganic salts, for example, sulfates (e.g., sodium sulfate, magnesium sulfate and zinc sulfate) or chlorides (e.g., sodium chloride). These inorganic salts are preferably used in an amount of 0 to 20% by weight based on the total composition.

The bathing preparation of the present invention may furthermore contain various additives commonly used in bathing preparations to thereby enhance the effects. Examples of these additives include pigments, vitamins, active ingredients of hot springs, proteases, marine algae extracts, sodium alginate, lanolin, silicones, crude drugs or extracts thereof, and so on.

The bathing preparation of the present invention can provide carbon dioxide gas dissolved in bath water by appropriately selecting the composition ratio between the organic acid(s) and carbonate(s) in such a manner as to adjust the pH value of the bath water to 5 to 7. It is expected, in this case, that the dissolved carbon dioxide gas accelerates blood circulation.

It is preferable that the bathing preparation of the present invention is formulated into tablets since the dissolution of the carbon dioxide gas in bath water can be promoted thereby. However, it may be formulated into other forms such as a powder or granules. During the formulation step, conventional vehicles or lubricants may be used, if required.

Specific examples of the vehicles include sodium chloride, kaolin, carboxyvinyl polymer, powdered licorice, light silicic anhydride, synthetic aluminum silicate, magnesium silicate, calcium citrate, crystal cellulose, D-sorbitol, talc, precipitated calcium carbonate, dextrin, starch, tragacanth, lactose, sucrose, dextrose, D-mannitol, magnesium aluminum oxide metasilicate, aluminum monstearate, medical soap, calcium phosphate, calcium hydrogenphosphate, calcium sulfate, gum arabic, glycerin, syrupus simplex, aromatic powders, water, etc.

Specific examples of the lubricants include carnauba wax, light silicic anhydride, magnesium silicate, synthetic aluminum silicate, hardened oils, white Japan wax, titanium oxide, stearic acid, stearic acid salts (e.g., Al, K, Na, Ca, Mg), talc, corn starch, microcrystalline cellulose, Macrogol-4000, Macrogol-6000, isopropyl myristate, magnesium lauryl sulfate, calcium hydrogenphosphate, waxes, colloidal silicates (e.g., magnesium aluminum oxide silicate), etc.

As described above, the bathing preparation of the present invention comprising organic acids, including fumaric acid, at a definite level or above sustains specific highly volatile perfumes in bath water without vaporization, thus giving desirable bathing effects.

The present invention is now illustrated in greater detail by way of the following Examples wherein perfumes A to K shown in Table 1 were employed, but it should be understood that the present invention is not deemed to be limited thereto.

TABLE 1

| Perfume | A | B | C | D | E | F | G | H | I | J | K |
|---|---|---|---|---|---|---|---|---|---|---|---|
| limonene | 60 | | | 40 | | | 52 | 40 | 70 | | 8 |
| pinene | 20 | | | | | | | 20 | | | |
| terpinolene | 20 | | | 10 | | | 10 | | | | 1 |
| geranyl formate | | 40 | | 20 | | 30 | | 1 | 1 | | |
| benzyl formate | | 30 | | | 10 | | | | | | |
| phenylethyl formate | | 30 | | 30 | | | | | | | |
| citronellyl acetate | | | 20 | | | 20 | 2 | | 1 | | 3 |
| geranyl acetate | | | 30 | | | | | 5 | 1 | | 3 |
| benzyl acetate | | | 10 | | 10 | 10 | | 1 | | | |
| phenylethyl acetate | | | 20 | | 30 | | 4 | | | | 1 |
| terpenyl acetate | | | 20 | | | | | | | | 3 |
| benzyl propionate | | | | 40 | 50 | | | | 1 | | 2 |
| isoamyl propionate | | | | 10 | | 40 | | | 2 | | |
| terpenyl propionate | | | | 50 | | | | | | | |
| lilial | | | | | | | | | 10 | | 15 |
| methyl dihydrodijasmonate | | | | | | | | | | 10 | 10 |
| cyclamen aldehyde | | | | | | | | 1 | | | 5 |
| isoamyl salicylate | | | | | | | | 2 | | | |
| methyl anthranilate | | | | | | | | 1 | | | 1 |
| methyl methylanthranilate | | | | | | | | | 1 | | 1 |
| methyl naphthyl ether | | | | | | | | 1 | | | |
| ethyl naphthyl ether | | | | | | | | | 1 | | 1 |
| tonalide | | | | | | | | | 4 | | |
| pentalide | | | | | | | | 4 | | | 10 |
| galaxolide | | | | | | | | 4 | 1 | 10 | 20 |
| ethyl vanillin | | | | | | | | 0.1 | | 1 | |
| anisic aldehyde | | | | | | | | | | 1 | |
| geraniol | | | | | | | | 5 | | | 8 |
| anethole | | | | | | | | | | 2 | 1 |
| phenylethyl alcohol | | | | | | | | 14.8 | 13 | | |
| terpineol | | | | | | | | | 1 | | |
| damascone | | | | | | | | 0.1 | | 0.5 | |
| ionone | | | | | | | | 1 | | | 5 |
| arylamyl glycolate | | | | | | | | | | 0.5 | |
| cis-3-hexenyl salicylate | | | | | | | | | | | 1 |

EXAMPLE 1

| Composition: | |
|---|---|
| Sodium Hydrogencarbonate | 43.8 (wt %) |
| Sodium Carbonate | 15 (wt %) |
| Organic Acids (Table 2) | 40 (wt %) |
| Dextrin | 0.8 (wt %) |
| Perfume A | 0.4 (wt %) |

A bathing preparation of the above composition was mixed and tableted. 50 g of the bathing preparation was introduced into a bath tub (910×710 cm) filled with 150 liters of water at 40° C. and the aroma was evaluated over the course of time by experienced panelists according to the following criterion:

○: full aroma;
◉: moderate aroma;
Δ: slight aroma; and
×: no aroma.

The evaluations ○ and ◉ were satisfactory as a bathing preparation.

The results are shown in Table 2 below.

TABLE 2

|  | No. 1 | No. 2 | No. 3 | No. 4 | No. 5 | No. 6 | No. 7 | No. 8 |
|---|---|---|---|---|---|---|---|---|
| Organic Acid (wt %) | | | | | | | | |
| succinic acid | 100 | 90 | 80 | 60 | 40 | 20 | 0 | 0 |
| fumaric acid | 0 | 10 | 20 | 40 | 60 | 80 | 100 | 20 |
| tartaric acid | 0 | 0 | 0 | 0 | 0 | 0 | 0 | 80 |
| Aroma | | | | | | | | |
| at disintegration | Δ | Δ | ○ | ○ | ○ | ○ | ○ | ○ |
| after 5 minutes | × | Δ | ◉ | ○ | ○ | ○ | ○ | ◉ |
| after 15 minutes | × | × | ◉ | ○ | ○ | ○ | ○ | ◉ |
| after 60 minutes | × | × | ◉ | ◉ | ○ | ○ | ○ | ◉ |

From the results shown in Table 2, it can be seen that the bathing preparation containing 20% by weight or more of fumaric acid as an organic acid sustains the aroma thereof for a prolonged period of time.

EXAMPLE 2

| Composition: | |
|---|---|
| Sodium Hydrogencarbonate | 43.8 (wt %) |
| Sodium Carbonate | 15 (wt %) |
| Organic Acids (Table 3) | 40 (wt %) |
| Dextrin | 0.8 (wt %) |
| Perfume (Table 3) | 0.4 (wt %) |

A bathing preparation of the above composition was mixed, tableted and introduced into a bath tub in the same manner as described in Example 1. 60 minutes after the introduction, the aroma of the bath water was evaluated by experienced panelists similar to Example 1.

The results are shown in Table 3 below.

TABLE 3

| Perfume | No. 9 B | No. 10 B | No. 11 C | No. 12 D | No. 13 E | No. 14 F | No. 15 G |
|---|---|---|---|---|---|---|---|
| Organic Acid (wt %) | | | | | | | |
| succinic acid | 90 | 50 | 50 | 50 | 50 | 50 | 50 |
| fumaric acid | 10 | 50 | 50 | 50 | 50 | 50 | 50 |
| Aroma after 60 min. | × | ○ | ◉ | ○ | ◉ | ○ | ○ |

From the results shown in Table 3, it can be seen that the bathing preparation containing 20% by weight or more (for example, 50% by weight) of fumaric acid as an organic acid sustains the aroma thereof for a prolonged period of time in spite of the kind of perfume.

EXAMPLE 3

A bathing preparation of the same composition as described in Example 2 but using the organic acids and perfumes shown in Table 4 was mixed, tableted and introduced into a bath tub similar to Example 1. 60 minutes after the introduction, the aroma of the bath water was organoleptically evaluated by experienced panelists in the same manner as the one described in Example 1.

The results are shown in Table 4 below.

TABLE 4

| Perfume | No. 16 H | No. 17 H | No. 18 I | No. 19 J | No. 20 K |
|---|---|---|---|---|---|
| Organic Acid (wt %) | | | | | |
| succinic acid | 100 | 40 | 40 | 40 | 40 |
| fumaric acid | 0 | 60 | 60 | 60*1 | 60*2 |
| Aroma after 60 min. | × | ◉ | ○ | ○ | ◉ |

Note:
*1 95.20 wt % of fumaric acid was surface-treated by a heat-molten process with 4.75 wt % of polyethylene glycol (average molecular weight: 6,000) and 0.05 wt % of sucrose fatty acid ester (HLB 15).
*2 88 wt % of fumaric acid was surface-treated by a spray drying process with 12 wt % of sodium polyacrylate (average molecular weight: 8,000).

From the results shown in Table 4, it can be seen that the bathing preparation containing 20% by weight or more (for example, 60% by weight) of fumaric acid as an organic acid sustains the aroma thereof for a prolonged period of time in spite of the kind of perfume.

While the invention has been described in detail and with reference to specific embodiments thereof, it will be apparent to one skilled in the art that various changes and modifications can be made therein without departing from the spirit and scope thereof.

What is claimed is:

1. A bathing preparation comprising:
(A) fumaric acid in combination with at least one other organic acid, wherein fumaric acid is present in amounts of 20% by weight or more of the total of said fumaric acid and said at least one other organic acid, wherein said fumaric acid is surface-treated with a water-soluble polymer, a hydrophilic nonionic surfactant or mixture thereof,
(B) at least one carbonate in an amount effective to yield sufficient carbonic acid gas to promote blood circulation,
(C) at least one perfume selected from the group consisting of terpene hydrocarbons having 10 carbon atoms and formates, acetates and propionates of an alcohol having from 5 to 10 carbon atoms, in an amount effective to impart sufficient aroma to the bathing preparation wherein said terpene hydrocarbons having 10 carbon atoms are selected from the group consisting of α-pinene, β-pinene, camphene, limonene, terpinolene, myrcene, and p-cymene; wherein said formates of an alcohol are selected from the group consisting of geranyl formate, benzyl formate and phenylethyl formate;

wherein said acetate of an alcohol is selected from the group consisting of isoamyl acetate, citronellyl acetate, geranyl acetate, benzyl acetate, linalyl acetate, phenylethyl acetate, methyl acetate, bornyl acetate, terpenyl acetate, cinnamyl acetate, anisyl acetate and myrcenyl acetate; and wherein said propionates of an alcohol are selected from the group consisting of linalyl propionate, cintronellyl propionate, geranyl propionate, benzyl propionate, terpenyl propionate and cinnamyl propionate, (D) wherein the water-soluble polymer is used in an amount of 0 to 40% by weight based on the fumaric acid and the hydrophilic nonionic surfactant is used in an amount of 0 to 5% by weight based on the fumaric acid.

2. The bathing preparation as claimed in claim 1, wherein said carbonate is selected from the group consisting of sodium hydrogencarbonate, sodium carbonate, potassium hydrogencarbonate, potassium carbonate, calcium carbonate, magnesium carbonate and sodium sesquicarbonate and mixtures thereof.

3. The bathing preparation as claimed in claim 1, wherein said carbonate is employed in an amount of from 5 to 80% by weight based upon the total composition.

4. The bathing preparation as claimed in claim 3, wherein said carbonate is employed in an amount of from 10 to 50% by weight based upon the total composition.

5. The bathing preparation as claimed in claim 1, wherein said organic acid is a mixture of fumaric acid and at least one organic acid selected from the group consisting of citric acid, succinic acid, malic acid and tartaric acid.

6. The bathing preparation as claimed in claim 1, wherein said organic acid is employed in an amount of from 10 to 300% by weight based upon said carbonate.

7. The bathing preparation as claimed in claim 6, wherein said organic acid is employed in an amount of from 30 to 150% by weight based upon said carbonate.

8. The bathing preparation as claimed in claim 1, wherein said perfume is employed in an amount of from 0.001 to 2% by weight based on the total composition.

9. The bathing preparation as claimed in claim 8, wherein said perfume is employed in an amount of from 0.005 to 0.6% by weight based on the total composition.

10. The bathing preparation as claimed in claim 1, wherein said carbonate is employed in an amount of from 5 to 80% by weight based upon the total composition, wherein said organic acid is employed in an amount of from 10 to 300% by weight based upon said carbonate, and wherein said perfume is employed in an amount of from 0.001 to 2% by weight based on the total composition.

11. The bathing preparation as claimed in claim 10, wherein said at least one organic acid is fumaric acid in combination with either succinic acid or tartaric acid.

12. The bathing preparation of claim 1, wherein said water-soluble polymer is at least one compound selected from the group consisting of sodium polyacrylate and sodium carboxymethyl cellulose, and said hydrophilic nonionic surfactant is at least one compound selected from the group consisting of polyethylene glycol, sucrose fatty acid esters, and polyglycerol fatty acid esters.

13. The bathing preparation of claim 1, wherein said water-soluble polymer amounts from 0.1 to 20% by weight based on fumaric acid and said hydrophilic nonionic surfactant amounts from 0.02 and 0.1% by weight based on fumaric acid.

14. The bathing preparation as claimed in claim 1, wherein the water-soluble polymer is used in an amount of 0.1 to 20% by weight based on the fumaric acid.

15. The bathing preparation as claimed in claim 1, wherein the hydrophobic nonionic surfactant is used in an amount of 0.02 to 0.1% by weight based on the fumaric acid.

16. The bathing preparation as claimed in claim 1, wherein the water-soluble polymer is used in an amount of 0.1 to 20% by weight based on the fumaric acid and the hydrophilic nonionic surfactant is used in an amount of 0.02 to 0.1% by weight based on the fumaric acid.

* * * * *